United States Patent
Narimatsu

(10) Patent No.: US 6,186,953 B1
(45) Date of Patent: Feb. 13, 2001

(54) NON-INVASIVE AND CONTINUOUS BLOOD-PRESSURE ESTIMATION APPARATUS

(75) Inventor: Kiyoyuki Narimatsu, Kasugai (JP)

(73) Assignee: Colin Corporation, Komaki (JP)

( * ) Notice: Under 35 U.S.C. 154(b), the term of this patent shall be extended for 0 days.

(21) Appl. No.: 09/398,457

(22) Filed: Sep. 17, 1999

(30) Foreign Application Priority Data

Oct. 29, 1998 (JP) ................................................ 10-308032

(51) Int. Cl.$^7$ ....................................................... A61B 5/02
(52) U.S. Cl. ........................ 600/485; 600/490; 128/925; 706/15
(58) Field of Search ................................... 600/481, 485, 600/486, 490, 493, 494, 495, 496, 500, 501, 502; 128/924, 925; 706/15, 16

(56) References Cited

U.S. PATENT DOCUMENTS

| | | | |
|---|---|---|---|
| 5,752,920 | * 5/1998 | Ogura et al. | 600/494 |
| 5,895,359 | * 4/1999 | Peel, III | 600/494 |
| 5,931,790 | * 8/1999 | Peel, III | 600/494 |
| 6,027,455 | * 2/2000 | Inukai et al. | 600/490 |
| 6,036,651 | * 3/2000 | Inukai et al. | 600/485 |
| 6,036,652 | * 3/2000 | Inukai et al. | 600/493 |

FOREIGN PATENT DOCUMENTS

U7-9305  2/1995 (JP) .
7-308295  11/1995 (JP) .

\* cited by examiner

*Primary Examiner*—Cary O'Connor
*Assistant Examiner*—Navin Natnithithadha
(74) *Attorney, Agent, or Firm*—Oliff & Berridge, PLC

(57) ABSTRACT

An apparatus for iteratively estimating an intra-arterial blood-pressure value of a living subject, including a first information obtaining device which non-invasively and iteratively obtains information relating to propagation of a pulse wave through an arterial vessel of the subject, a second information obtaining device which non-invasively and iteratively obtains information relating to heartbeat of the subject and/or information relating to area of a heartbeat-synchronous pulse of a volumetric pulse wave obtained from a peripheral body portion of the subject, and an estimating device including a neural network which learns sets of information each set of which includes a blood-pressure value measured using a cuff, pulse-wave-propagation-relating information obtained when the blood-pressure value is measured using the cuff, and heartbeat-relating information and/or pulse-wave-area-relating information obtained when the blood-pressure value is measured using the cuff, the neural network iteratively estimating an intra-arterial blood-pressure value of the subject, based on each piece of pulse-wave-propagation-relating information iteratively obtained by the first information obtaining device, and each piece of heartbeat-relating information and/or each piece of pulse-wave-area-relating information which are or is iteratively obtained by the second information obtaining device.

13 Claims, 8 Drawing Sheets

NON-INVASIVE AND CONTINUOUS BLOOD-PRESSURE ESTIMATION APPARATUS

BACKGROUND OF THE INVENTION

1. Field of the Invention

The present invention relates to an apparatus for iteratively estimating an intra-arterial blood-pressure value of a living subject, based on information non-invasively obtained from a circulatory system of the subject.

2. Related Art Statement

There is known an automatic blood-pressure ("BP") measuring device which non-invasively measures an intra-arterial BP value of a living subject, such as a "Korotkoff-sound-type" BP measuring device or an "oscillometric-type" BP measuring device. The Korotkoff-sound-type BP measuring device determines a BP value of a subject based on the first and/or last detection of Korotkoff sounds produced when a pressing pressure of a pressing belt wrapped around a body portion of the subject is changed, and the oscillometric-type BP measuring device determines a BP value of a subject based on variation of respective amplitudes of heartbeat-synchronous pulses produced when a pressing pressure of a pressing belt is changed.

Meanwhile, in an operation room or an intensive care unit, it may be required to periodically measure a BP value of a patient at the shortest possible period, so that a medical staff can give one or more urgent treatments to the patient. However, in the above-indicated prior BP measuring device, no BP values can be obtained before several tens of seconds have passed from the commencement of operation of the measuring device. In the case where a BP value of a patient is periodically measured at a very short period, the body portion of the patient around which the pressing belt is wrapped may suffer congestion due to the frequency compression of the pressing belt, and the obtained BP values may include errors due to the congestion of the patient.

In this background, there has been proposed a non-invasive and continuous BP estimation device which calculates, based on a signal non-invasively obtained from a living subject, a velocity at which a pulse wave propagates through an arterial vessel of the subject, and continuously estimates a BP value of the subject based on the calculated velocity according to a predetermined relationship. This BP estimation device is disclosed in, e.g., Japanese Utility Model Application laid open for inspection purposes under Publication No. 7(1995)-9305 and Japanese Patent Application laid open for inspection purposes under Publication No. 7-308295.

However, the above-identified BP estimation device estimates a BP value based on only a pulse-wave propagation velocity or a pulse-wave propagation time, and accordingly cannot enjoy a satisfactory accuracy of estimation of BP values. Thus, the prior BP estimation device needs to frequently calibrate itself based on one or more BP values measured by a Korotkoff-sound-type or oscillometric automatic BP measuring device using a pressing belt.

SUMMARY OF THE INVENTION

It is therefore an object of the present invention to provide a non-invasive and continuous blood-pressure estimation apparatus which can estimate blood pressure values of a living subject with a high accuracy.

The present invention provides a blood-pressure estimating apparatus which has one or more of the technical features that are described below in respective paragraphs given parenthesized sequential numbers (1) to (13). Any technical feature which includes another technical feature shall do so by referring, at the beginning, to the parenthesized sequential number given to that technical feature.

(1) According to a first feature of the present invention, there is provided an apparatus for iteratively estimating an intra-arterial blood-pressure value of a living subject, based on information non-invasively obtained from a circulatory system of the subject, the apparatus comprising a pulse-wave-propagation-relating-information obtaining device which non-invasively and iteratively obtains a piece of pulse-wave-propagation-relating information relating to propagation of a pulse wave through an arterial vessel of the living subject; a circulation-relating-information obtaining device which non-invasively and iteratively obtains a piece of circulation-relating information comprising at least one of a piece of heartbeat-relating information relating to heartbeat of the living subject and a piece of pulse-wave-area-relating information relating to area of a heartbeat-synchronous pulse of a volumetric pulse wave obtained from a peripheral body portion of the living subject; and blood-pressure estimating means comprising a neural network which learns a plurality of sets of information each set of which comprises a blood-pressure value measured using an inflatable cuff, a piece of pulse-wave-propagation-relating information obtained when the blood-pressure value is measured using the cuff, and at least one of a piece of heartbeat-relating information obtained when the blood-pressure value is measured using the cuff and a piece of pulse-wave-area-relating information obtained when the blood-pressure value is measured using the cuff, the neural network iteratively estimating an intra-arterial blood-pressure value of the living subject, based on each piece of pulse-wave-propagation-relating information iteratively obtained by the pulse-wave-propagation-relating-information obtaining device and at least one of each piece of heartbeat-relating information and each piece of pulse-wave-area-relating information which is iteratively obtained by the circulation-relating-information obtaining device. The present BP estimating apparatus estimates a BP value of a living subject such as a patient based on not only the pulse-wave-propagation-relating information but also at least one of the heartbeat-relating information as a parameter which relates to the central portion of the circulatory system of the subject and changes in relation to the BP of the subject and the pulse-wave-area-relating information which relates to a peripheral portion of the circulatory system of the subject and changes in relation to the BP of the subject. Thus, the present apparatus can more accurately estimate BP values of the subject than a conventional apparatus which estimates a BP value of a living subject based on pulse-wave-propagation-relating information only.

(2) According to a second feature of the present invention that includes the first feature (1), the blood-pressure estimating apparatus further comprises a blood-pressure measuring device which includes an inflatable cuff adapted to apply a pressing pressure to a body portion of the living subject and which measures a blood-pressure value of the living subject by changing the pressing pressure of the inflatable cuff, and the blood-pressure estimating means further comprises modifying means for modifying the neural network based on comparison of the blood-pressure value of the living subject measured by the measuring device, and the blood-pressure value of the subject estimated by the blood-pressure estimating means when the blood-pressure value is measured by the blood-pressure measuring device. In the present BP estimating apparatus, the modifying means modifies the neural network, so that the neural network is adapted for an individual living subject such as an individual patient. Thus, the present apparatus can more accurately estimate BP values of the subject.

(3) According to a third feature of the present invention that includes the first or second feature (1) or (2), the neural network learns the plurality of sets of information each set of which comprises the blood-pressure value measured using the inflatable cuff, the piece of pulse-wave-propagation-relating information obtained when the blood-pressure value is measured using the cuff, the piece of heartbeat-relating information obtained when the blood-pressure value is measured using the cuff, and the piece of pulse-wave-area-relating information obtained when the blood-pressure value is measured using the cuff, and wherein the blood-pressure estimating means iteratively estimates an intra-arterial blood-pressure value of the living subject, based on each piece of pulse-wave-propagation-relating information iteratively obtained by the pulse-wave-propagation-relating-information obtaining device, and each piece of heartbeat-relating information and each piece of pulse-wave-area-relating information which are iteratively obtained by the circulation-relating-information obtaining device. The present BP estimating apparatus estimates a BP value of a subject based on not only the pulse-wave-propagation-relating information but also both the heartbeat-relating information as the parameter which relates to the central portion of the circulatory system of the subject and changes in relation to the BP of the subject and the pulse-wave-area-relating information which relates to the peripheral portion of the circulatory system of the subject and changes in relation to the BP of the subject. Thus, the present apparatus can more accurately estimate BP values of the subject than the conventional apparatus which estimates a BP value of a subject based on pulse-wave-propagation-relating information only.

(4) According to a fourth feature of the present invention that includes any one of the first to third features (1) to (3), the neural network comprises an input layer including at least two input-layer elements, at least one intermediate layer including at least two intermediate-layer elements, and an output layer including an output-layer element, each of the input-layer elements being connected to each of the intermediate-layer elements, with a corresponding one of a plurality of first connection factors, each of the intermediate-layer elements being connected to the output-layer element, with a corresponding one of a plurality of second connection factors, and wherein when a value is transferred from the each input-layer element to the each intermediate-layer element, the value is multiplied with the one first connection factor and then is plus a corresponding one of first offset values, and when a value is transferred from the each intermediate-layer element to the output-layer element, the value is multiplied with the one second connection factor and then is plus a corresponding one of second offset values.

(5) According to a fifth feature of the present invention that includes the fourth feature (4), each of the intermediate-layer elements outputs an output value based on a sum of respective input values received from the input-layer elements and a first transfer function, and the output-layer element outputs an output value based on a sum of respective input values received from the intermediate-layer elements and a second transfer function.

(6) According to a sixth feature of the present invention that includes the fourth or fifth feature (4) or (5), the blood-pressure estimating apparatus further comprises a blood-pressure measuring device which includes an inflatable cuff adapted to apply a pressing pressure to a body portion of the living subject and which measures a blood-pressure value of the living subject by changing the pressing pressure of the inflatable cuff, wherein the blood-pressure estimating means further comprises modifying means for modifying the first and second connection factors and the first and second offset values of the neural network based on a difference of the blood-pressure value of the living subject measured by the blood-pressure measuring device, and the blood-pressure value of the subject estimated by the blood-pressure estimating means when the blood-pressure value is measured by the blood-pressure measuring device.

(7) According to a seventh feature of the present invention that includes the sixth feature (6), the blood-pressure estimating means further comprises initializing means for initializing the modified first and second connection factors and the modified first and second offset values of the neural network, to the first and second connection factors and the first and second offset values before being modified by the modifying means, when a state in which a difference of a current blood-pressure value measured by the measuring device and a blood-pressure value estimated by the blood-pressure estimating means when the current blood-pressure value measured by the measuring device is greater than a difference of a preceding blood-pressure value measured by the measuring device and a blood-pressure value estimated by the blood-pressure estimating means when the preceding blood-pressure value is measured by the measuring device, continues for a predetermined number of blood-pressure measurements of the blood-pressure measuring device.

(8) According to an eighth feature of the present invention that includes any one of the first to seventh features (1) to (7), the blood-pressure estimating apparatus further comprises a blood-pressure measuring device which includes an inflatable cuff adapted to apply a pressing pressure to a body portion of the living subject and which measures a blood-pressure value of the living subject by changing the pressing pressure of the inflatable cuff; and starting means for starting a blood-pressure measurement of the blood-pressure measuring device when the blood-pressure value of the living subject estimated by the blood-pressure estimating means is abnormal.

(9) According to a ninth feature of the present invention that includes any one of the first to eighth features (1) to (8), the blood-pressure estimating apparatus further comprises an informing device which informs a user of an occurrence of an abnormality to the blood pressure of the living subject, when the blood-pressure value of the living subject estimated by the blood-pressure estimating means is abnormal.

(10) According to a tenth feature of the present invention that includes any one of the first to ninth features (1) to (9), the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

(11) According to an eleventh feature of the present invention that includes any one of the first to tenth features (1) to (10), the pulse-wave-propagation-relating-information obtaining device comprises an electro-cardiographic-pulse-wave detecting device which includes a plurality of electrodes adapted to be put on a plurality of portions of the living body and detects an electro-cardiographic pulse wave including a plurality of heartbeat-synchronous pulses, from the subject via the electrodes, and a photoelectric-pulse-wave detecting device which is adapted to be worn on a body portion of the living subject, and which emits a light toward the body portion and obtains a photoelectric pulse wave including a plurality of heartbeat-synchronous pulses, from the light received from the body portion.

(12) According to a twelfth feature of the present invention that includes the eleventh feature (11), the circulation-relating-information obtaining device comprises a heartbeat-relating-information obtaining device which non-invasively and iteratively obtains a piece of heartbeat-relating information, and wherein the heartbeat-relating-information obtaining device comprises pulse-period calculating means for iteratively calculating, as the piece of heartbeat-relating information, a pulse period equal to an interval between each pair of successive heartbeat-synchronous pulses of the electrocardiographic pulse wave detected by the electrocardiographic-pulse-wave detecting device.

(13) According to a thirteenth feature of the present invention that includes the eleventh or twelfth feature (11) or (13), the circulation-relating-information obtaining device comprises a pulse-wave-area-relating-information obtaining device which non-invasively and iteratively obtains a piece of pulse-wave-area-relating information, and wherein the pulse-wave-area-relating-information obtaining device comprises ratio calculating means for iteratively calculating, as the piece of pulse-wave-area-relating information, a ratio of an area defined by a waveform of each heartbeat-synchronous pulse of the photoelectric pulse wave as the volumetric pulse wave to a pulse period equal to an interval between each pair of successive heartbeat-synchronous pulses of the electrocardiographic pulse wave detected by the electrocardiographic-pulse-wave detecting device.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
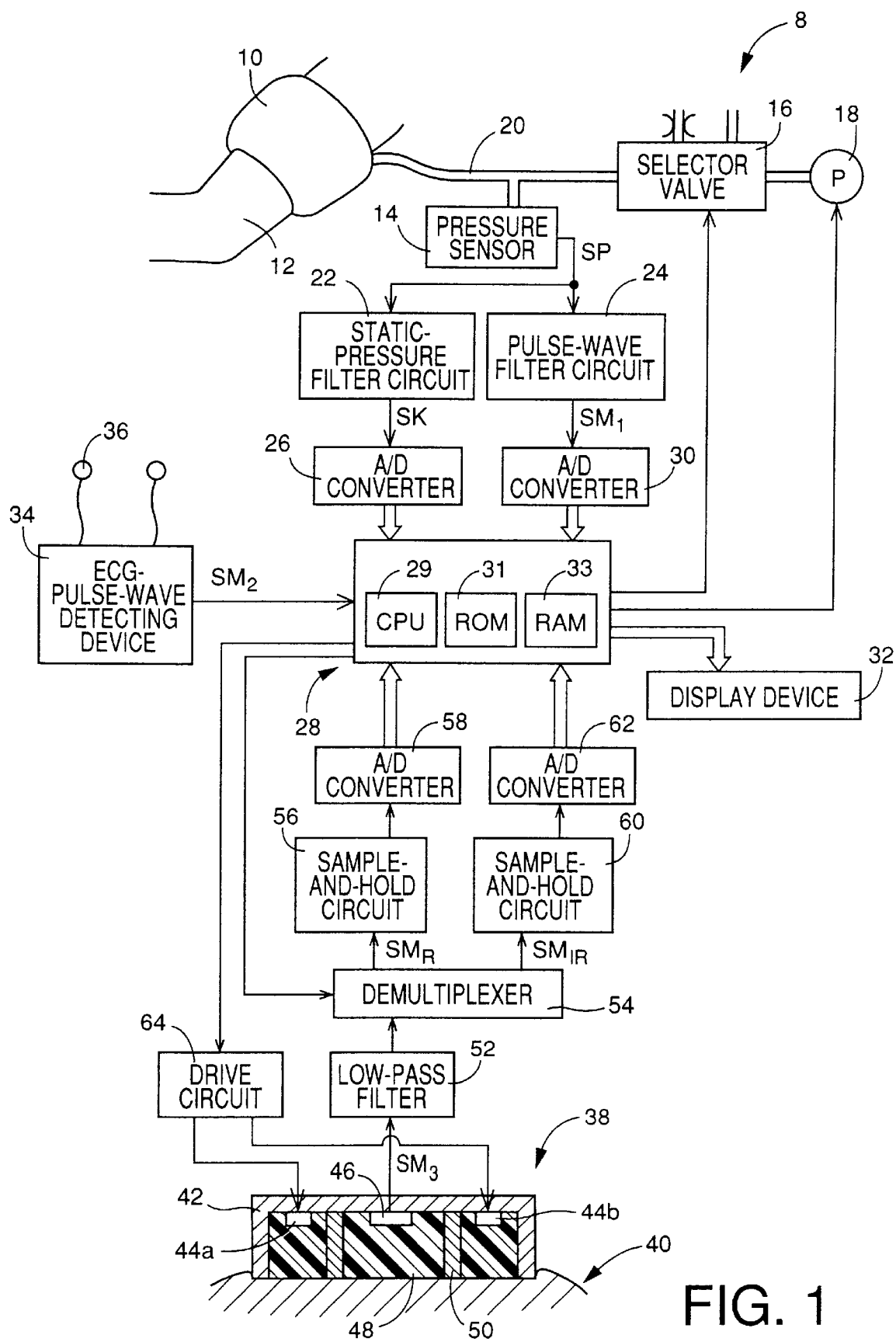
FIG. 1 is a diagrammatic view of a non-invasive and continuous blood-pressure ("BP") estimation apparatus embodying the present invention.

Referring to FIG. 1, there will be described a non-invasive and continuous blood-pressure ("BP") estimation apparatus 8 embodying the present invention.

In FIG. 1, the BP estimation apparatus 8 includes an inflatable cuff 10 which has a belt-like cloth bag and a rubber bag accommodated in the cloth bag and which is adapted to be wrapped around, e.g., a right upper arm 12 of a patient as a living subject, and a pressure sensor 14, a selector valve 16 and an air pump 18 each of which is connected to the cuff 10 via piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the inflatable cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff-pressure signal SK representative of the static cuff pressure. The cuff-pressure signal SK is supplied to an electronic control device 28 via an analog-to-digital ("A/D") converter 26. The pulse-wave filter circuit 24 includes a band-pass filter and extracts, from the pressure signal SP, an oscillatory component having predetermined frequencies, i.e., cuff-pulse-wave signal $SM_1$. The cuff-pulse-wave signal $SM_1$ is supplied to the control device 28 via an A/D converter 30. The cuff-pulse-wave signal $SM_1$ is representative of the cuff pulse wave, i.e., oscillatory pressure wave which is produced from a brachial artery (not shown) of the patient in synchronism with the heartbeat of the patient and is propagated to the inflatable cuff 10.

The control device 28 is provided by a so-called microcomputer including a central processing unit ("CPU") 29, a read only memory ("ROM") 31, a random access memory ("RAM") 33, and an input-and-output ("I/O") port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP estimation apparatus 8 further includes an electrocardiographic (ECG) pulse wave detecting device 34 which continuously detects an ECG pulse wave representative of the action potential of cardiac muscle of the patient, through a plurality of electrodes 36 being put on predetermined body portions of the patient, and supplies an ECG-pulse-wave signal $SM_2$ representative of the detected ECG pulse wave, to the control device 28. The ECG-pulse-wave detecting device 34 is used for detecting a Q-wave or an R-wave of each heartbeat-synchronous pulse of the ECG pulse wave that corresponds to a time point when the outputting of blood from the heart of the patient toward the aorta is started. Thus, the ECG-pulse-wave detecting device 34 functions as a first pulse-wave detecting device.

The BP estimation apparatus 8 further includes a photoelectric-pulse-wave detecting probe 38 (hereinafter, referred to as the "probe" 38) which is employed as part of a pulse oximeter. The probe 38 functions as a second pulse-wave detecting device, or a peripheral-pulse-wave detecting device for detecting a peripheral pulse wave propagated to a peripheral artery including capillaries. The probe 38 is set on a skin or a body surface 40 of the patient, e.g., an end portion of a finger of a left hand of the patient with the help of a band (not shown), such that the probe 38 is held in close contact with the body surface 40. The probe 38 is worn on the hand of one arm different from the other arm around which the cuff 10 is wrapped.

The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second groups of light emitting elements 44a, 44b, need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shading member 50 which is disposed between the light emitting elements 44 and the light receiving element 46, for preventing the light receiving element 46 from receiving the lights emitted toward the body surface 40 by the light emitting elements 44 and directly reflected from the body surface 40.

The first group of light emitting elements 44a emit a first light having a first wavelength $\lambda_1$ whose absorbance changes depending on a blood oxygen saturation value of the patient. The first elements 44a emit, e.g., a red light having about 660 nm wavelength. The second group of light emitting elements 44b emit a second light having a second wavelength $\lambda_2$ whose absorbance does not change depending on the blood oxygen saturation value of the patient. The second elements 44b emit, e.g., an infrared light having about 800 nm wavelength. The first and second light emitting elements 44a, 44b alternately emit the red and infrared lights, respectively, at a predetermined frequency, e.g., a relatively high frequency of several hundred Hz to several thousand Hz. The lights emitted toward the body surface 40 by the light emitting elements 44 are reflected from a body tissue of the patient where a dense capillaries occur, and the reflected lights are received by the common light receiving element 46. In place of the 660 nm and 800 nm lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric-pulse-wave signal $SM_3$ representative of an amount of the first or second light received from the body tissue of the patient. The light receiving element 46 is connected to the low-pass filter 52 via an amplifier or the like. The low-pass filter 52 removes, from the photoelectric-pulse-wave signal $SM_3$ input thereto, noise having frequencies higher than that of a pulse wave, and outputs the noise-free signal $SM_3$ to a demultiplexer 54. The photoelectric-pulse-wave signal $SM_3$ is representative of a photoelectric pulse wave as a volumetric pulse wave which is produced in synchronism with the arterial pulsation of the patient.

The demultiplexer 54 is switched according to signals supplied thereto from the control device 28 in synchronism with the alternate light emissions of the first and second light emitting elements 44a, 44b. Thus, the demultiplexer 54 separates the photoelectric-pulse-wave ("PPW") signal $SM_3$ into two PPW signals which correspond to the first and second lights, respectively. More specifically described, the demultiplexer 54 successively supplies, to the I/O port (not shown) of the control device 28, a first PPW signal $SM_R$ representative of the red light having the first wavelength $\lambda_1$ through a first sample-and-hold circuit 56 and an A/D converter 58, and a second PPW signal $SM_{IR}$ representative of the infrared light having the second wavelength $\lambda_2$ through a second sample-and-hold circuit 60 and an A/D converter 62. The first and second sample-and-hold circuits 56, 60 hold the first and second PPW signals $SM_R$, $SM_{IR}$ input thereto, respectively, and do not output those current signals to the A/D converters 58, 62, before the prior signals $SM_R$, $SM_{IR}$ are completely converted by the A/D converters 58, 62, respectively.

In the control device 28, the CPU 29 carries out a measuring operation according to control programs pre-stored in the ROM 31 by utilizing the temporary-storage function of the RAM 33. More specifically described, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions of the first and second light emitting elements 44a, 44b, the CPU 29 generates a switch signal SC to the demultiplexer 54 to switch the demultiplexer 54 between its first and second positions. Thus, the PPW signal $SM_3$ is separated by the demultiplexer 54 such that the first PPW signal $SM_R$ is supplied to the first sample-and-hold circuit 56 while the second PPW signal $SM_{IR}$ is supplied to the second sample-and-hold circuit 60.

Figure 2:
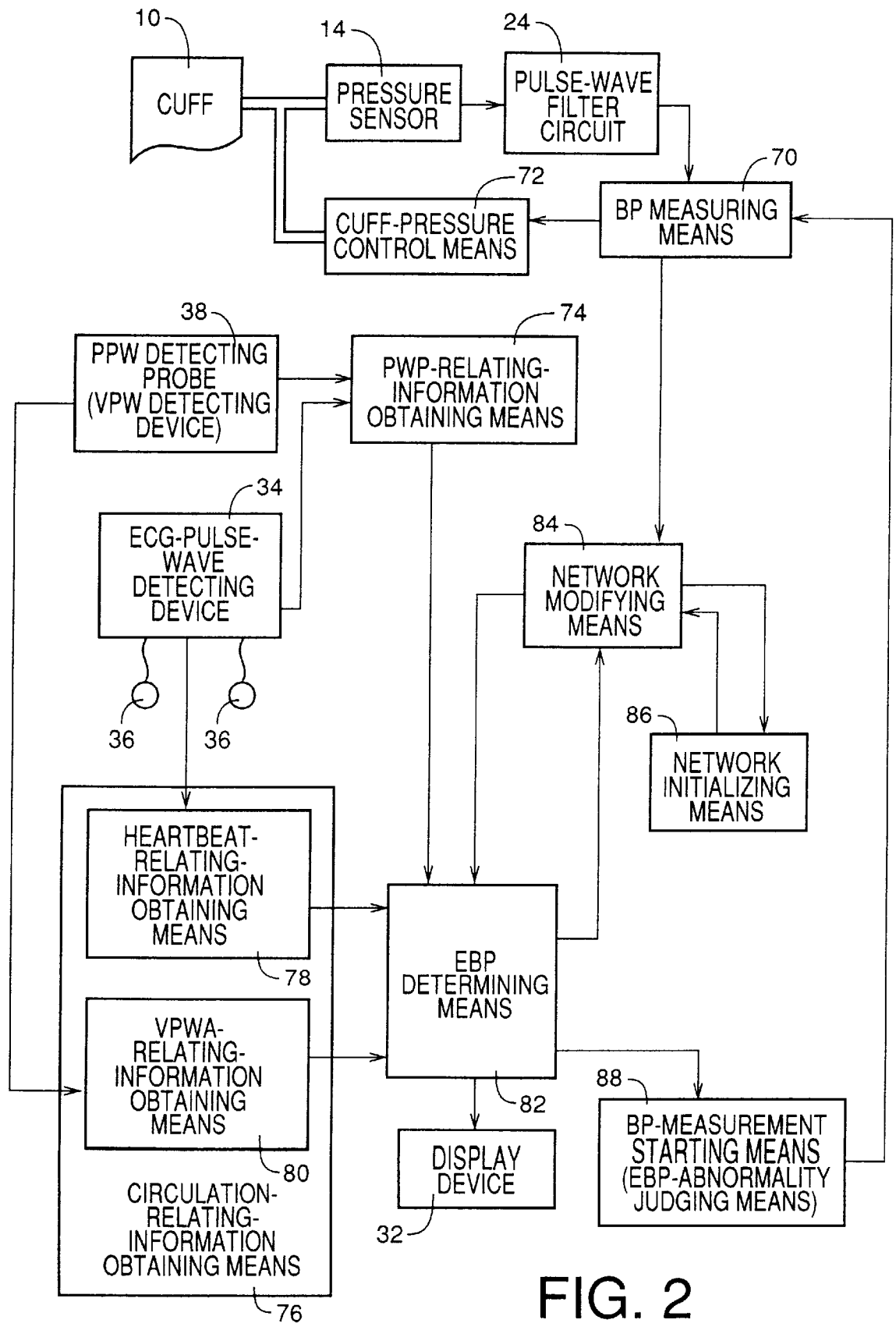
FIG. 2 is a block diagram for illustrating essential functions of an electronic control device of the apparatus of FIG. 1.

FIG. 2 illustrates essential functions of the control device 28 of the present BP estimation apparatus 8. In the figure, a BP measuring means or circuit 70 measures a systolic, a mean, and a diastolic BP value $BP_{SYS}$, $BP_{MEAN}$, $BP_{DIA}$ of the patient, according to a well known oscillometric method, based on the variation of respective amplitudes of heartbeat-synchronous pulses of the pulse wave represented by the cuff-pulse-wave signal $SM_1$ obtained while the cuff pressure which is quickly increased by a cuff-pressure control means or circuit 72 to a target pressure value $P_{CM}$ (e.g., 180 mmHg), is slowly decreased at the rate of about 3 mmHg/sec.

Figure 3:
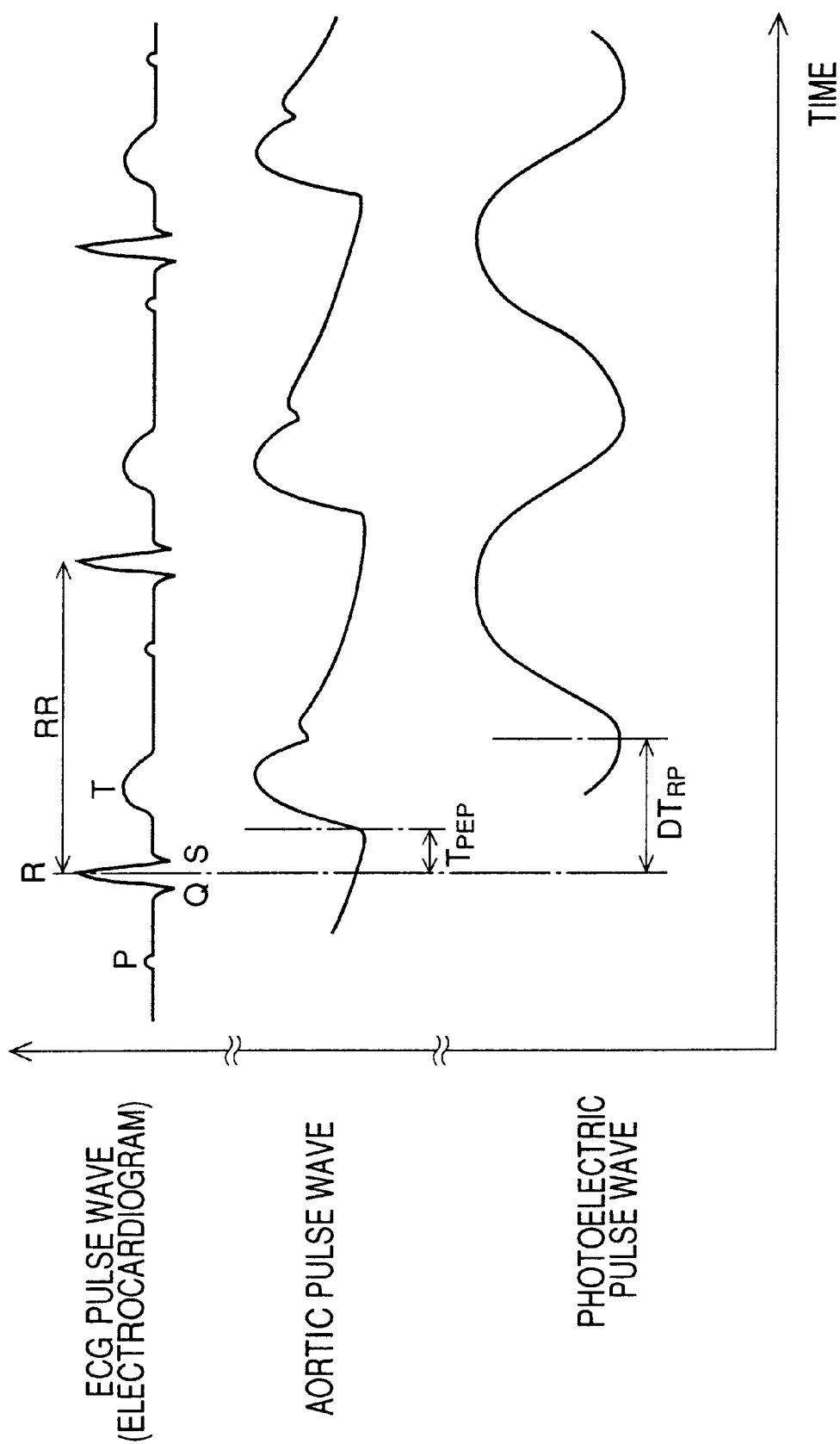
FIG. 3 is a view for illustrating a pulse-wave-propagation time $DT_{RP}$ obtained by an operation of the control device of the apparatus of FIG. 1.

A pulse-wave-propagation ("PWP") relating information obtaining means or circuit 74 includes a time-difference calculating means or circuit which non-invasively and iteratively calculates, as a PWP time $DT_{RP}$, a time difference between a predetermined point (e.g., R-wave) on the waveform of each of periodic pulses of the ECG pulse wave that are successively detected by the ECG-pulse-wave detecting device 34 and a predetermined point (e.g., rising point, i.e., minimum point) on the waveform of a corresponding one of periodic pulses of the photoelectric pulse wave ("PPW") detected by the probe 38, as illustrated in FIG. 3. The PPW-relating-information obtaining means 74 iteratively calculates a PWP velocity $V_M$ (m/sec) of a pulse wave which propagates through an artery of the patient, based on the calculated PPW time $DT_{RP}$, according to the following expression (1) pre-stored in the ROM 31:

$$V_M = L/(DT_{RP} - T_{PEP}) \tag{1}$$

where

L (m) is a length of the artery as measured from the left ventricle to the position where the probe 38 is set, via the aorta; and $T_{PEP}$ (sec) is a pre-ejection period between the R-wave of the waveform of each pulse of the ECG pulse wave and the minimum point of the waveform of a corresponding pulse of an aortic pulse wave.

The values L, $T_{PEP}$ are constants, and are experimentally obtained in advance.

Figure 4:
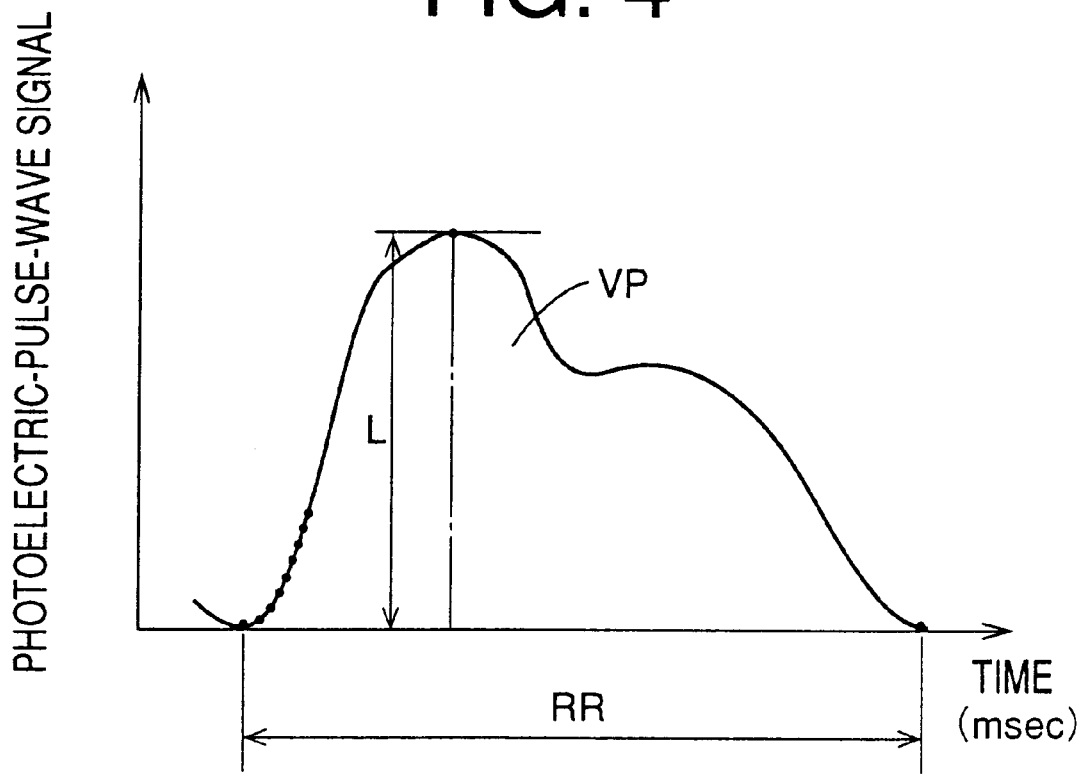
FIG. 4 is a view for explaining a manner in which a volumetric-pulse-wave-area relating value, such as a volumetric pulse wave area VP itself, is calculated.

A circulation-relating-information obtaining means or circuit 76 non-invasively and iteratively obtains at least one piece of circulation-relating information, and includes at least one of a heartbeat-relating-information obtaining means or circuit 78 and a pulse-wave-area-relating-information obtaining means or circuit 80. The heartbeat-relating-information obtaining means 78 non-invasively and iteratively obtains a piece of heartbeat-relating information relating to a heartbeat of the patient, such as a heart rate HR (i.e., pulse rate) or a pulse period RR (i.e., heartbeat period), and the pulse-wave-area-relating-information obtaining means or circuit 80 non-invasively and iteratively obtains a piece of pulse-wave-area-relating information relating to an area of each of heartbeat-synchronous pulses of a volumetric pulse wave detected from a peripheral body portion (e.g., finger) of the patient. A piece of pulse-wave-area-relating information may be an area VP of each pulse, a ratio VR of the area VP to the inverse of a pulse period RR (VR=VP/RR), a product VR' of the ratio VR and an amplitude L of the each pulse (VR'=VR×L), or a normalized pulse-wave area NV obtained by dividing the area VP by the product of the pulse period RR and the amplitude LL (NV=VP/(RR× L)). As shown in FIG. 4, the waveform of each pulse of the PPW (i.e., PPW signal $SM_3$) detected by the probe 38 is defined by a series of data points indicative of respective magnitudes which are input at a predetermined short interval such as several milliseconds to several tens of milliseconds. The area VP of each pulse of the PPW is obtained by integrating, over the period RR of the each pulse, respective magnitudes of the data points of the each pulse. Both the heartbeat-relating information and the pulse-wave-area-relating information change in relation to the change of the BP of the patient. More specifically described, the change of the BP of the patient is caused by the change of cardiac output in the central portion of the circulatory system of the patient, and by the change of blood-vessel resistance in a peripheral portion of the circulatory system. The heartbeat-relating information reflects the cardiac output, and the pulse-wave-area-relating information reflects the blood-vessel resistance.

An estimated-BP ("EBP") determining means or circuit 82 iteratively determines and outputs an estimated intra-arterial BP value EBP of the patient, by inputting input signals including each piece of PWP-relating information iteratively obtained by the PWP-relating-information obtaining means 74, and at least one of each piece of heartbeat-relating information and each piece of pulse-wave-area-relating information iteratively obtained by the circulation-relating-information obtaining means 76, into a neural network NN which has a prescribed architecture and which has learned a number (e.g., hundred) of sets of physical information each set of which includes a BP value measured from a living subject using a "data-collect" cuff which may, or may not, be identical with the "monitor" cuff 10, a piece of PWP-relating information obtained from that subject when the BP value is measured using the data-collect cuff, and at least one of a piece of heartbeat-relating information and a piece of pulse-wave-area-relating information obtained from that subject when the BP value is measured using the data-collect cuff.

The neural network NN employed in the EBP determining means 82 models a group of nerve cells (i.e., neurons) of a human being, and has a hierarchical-type network. Alternatively, the EBP determining means 82 may employ an interconnection-type neural network. The neural network NN learns, as a teacher signal, each BP value measured using the data-collect cuff, and simultaneously learns, as input signals, each piece of PWP-relating information when the BP value is measured using the data-collect cuff, and at least one of each piece of heartbeat-relating information and each piece of pulse-wave-area-relating information obtained when the BP value is measured using the data-collect cuff. Therefore, in the case where a systolic BP value is learned as a teacher signal, the neural network NN outputs an estimated systolic BP value $EBP_{SYS}$, and in the case where a mean or diastolic BP value is learned as a teacher signal, the neural network NN outputs an estimated mean or diastolic BP value $EBP_{MEAN}$ or $EBP_{DIA}$.

The above-indicated number of sets of physical information are the data which have been collected from a corresponding number of unspecified living subjects. Therefore, an average and accordingly accurate EBP value can be determined. However, the number of sets of physical information may be collected from specified subjects, e.g., subjects having a particular disease, a particular age or ages, or particular disease and age, or patients treated in intensive care units ("ICU"). In the latter case, a more accurate EBP value can be determined for a patient who is classified into those specified subjects.

Figure 5:
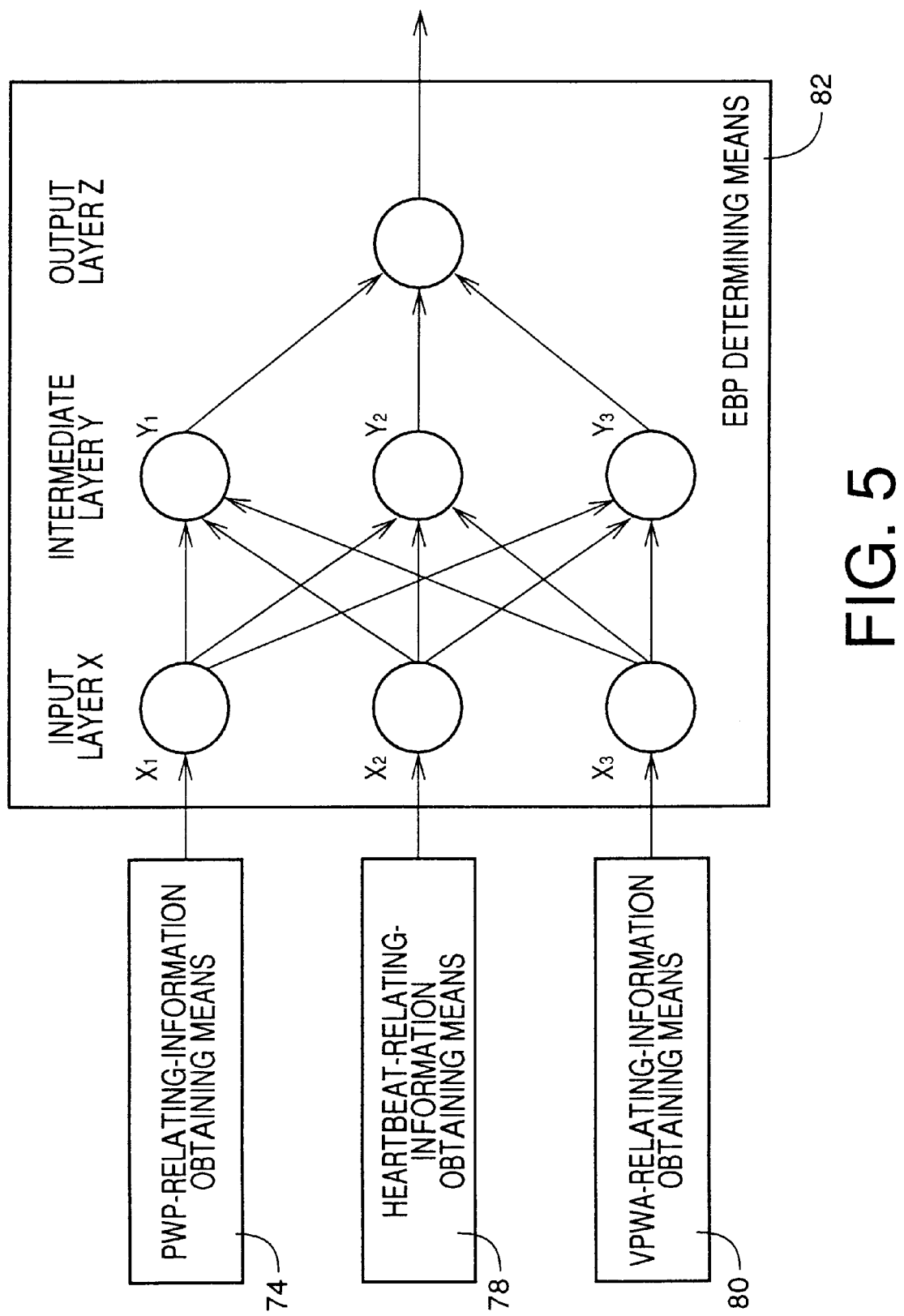
FIG. 5 is a view for illustrating a neural network NN which is employed in the apparatus of FIG. 1.

FIG. 5 shows an example of the neural network NN employed in the EBP determining means 82. This neural network NN is a hierarchical network including three layers, i.e., an input layer X, a single intermediate layer Y, and an output layer Z. The input layer X includes three units (i.e., neurons) $X_i$ (i=1 to 3), and the intermediate layer Y also includes three units (i.e., neurons) $Y_j$ (j=1 to 3). Each of the three input-layer units $X_i$ is connected to each of the three intermediate-layer units $Y_j$, with a connection coefficient (or weight) $W_{ij}$. Each of the three intermediate-layer units $Y_j$ is connected to a single output-layer unit $Z_k$ (k=1), with a connection coefficient (or weight) $V_{jk}$.

Figure 6:
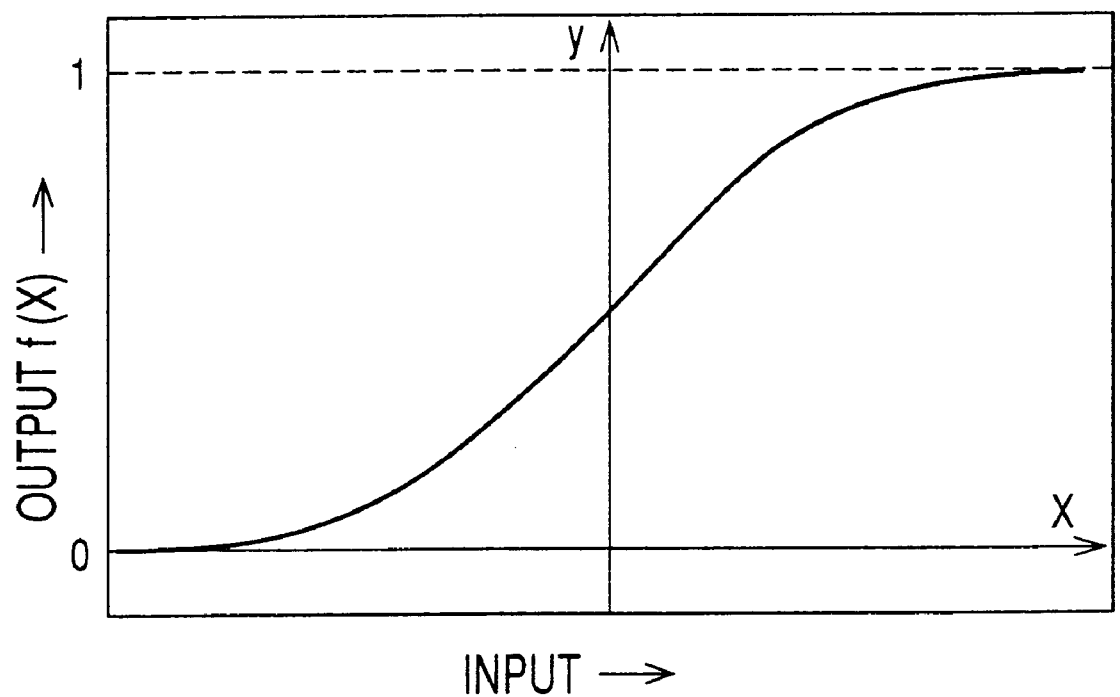
FIG. 6 is a graph for illustrating a sigmoid function which is utilized by the neural network of FIG. 5.

In the neural network NN shown in FIG. 5, each piece of PWP-relating information, each piece of heartbeat-relating information, and each piece of VPWA-relating information are input as three input signals to the three input-layer units $X_i$, respectively. Each input signal is multiplied by the connection coefficient $W_{ij}$, and then is plus an offset value $\Theta_j$ prescribed for each intermediate-layer unit $Y_j$. Thus, three inputs $U_{ij}$ to each intermediate-layer unit $Y_j$ are determined. Subsequently, an output $H_j$ of each intermediate-layer unit $Y_j$ is determined as the product of the sum of the three inputs $U_{ij}$ and a prescribed transfer function, e.g., a sigmoid function f(x) represented by the following expression (2) and illustrated in FIG. 6:

$$f(x) = 1/(1+\exp(-x)) \tag{2}$$

where x is a parameter.

Each output $H_j$ is multiplied by the connection coefficient $V_{jk}$, and then is plus an offset value $\gamma_k$ prescribed for the output-layer unit $Z_k$. Thus, three inputs $S_{jk}$ to the output-layer unit $Z_k$ are determined. Subsequently, an output $O_k$ of the output-layer unit $Z_k$ is determined as the product of the sum of the three inputs $S_{jk}$ and the sigmoid function f(x). An EBP value is determined by multiplying the output $O_k$ by a predetermined conversion factor A.

A network modifying means or circuit 84 modifies the neural network NN based on the comparison between the BP value measured by the BP measuring means 70, and the EBP value determined by the EBP determining means 82 when the BP value is measured by the BP measuring means 70. For example, regarding the hierarchical neural network NN shown in FIG. 5, the network modifying means 84 modifies, according to the well-known back-propagation method, the connection factors $W_{ij}$, the connection factors $V_{jk}$, the offsets $\Theta_j$, and the offset $\gamma_k$, so as to reduce or zero a difference or error $\delta$ between the BP value measured by the BP measuring means 70 (i.e., teacher signal T), and the EBP value determined by the EBP determining means 82 when the BP value is measured by the BP measuring means 70. The EBP value determined by the EBP determining means 82 when the BP value is measured by the BP measuring means 70, means an EBP determined based on a piece of PWP-relating information and at least one of a piece of heartbeat-relating information and a piece of pulse-wave-area-relating information all of which are obtained immediately before the inflatable cuff 10 is inflated for measuring the BP value, during a time period in which the cuff 10 is inflated, or immediately after the cuff 10 is deflated.

A network initializing means or circuit 86 judges, when a state in which an error $\delta$ calculated by the modifying means 84 is greater than the preceding error $\delta$ calculated immediately prior to the each error $\delta$ has continued for not less than a predetermined number of successive BP measuring operations, that the modifying of the neural network NN by the neural network modifying means 84 is abnormal, and initializes the modified neural network NN to its initial state before being modified by the modifying means 84. Thus, the neural network NN is prevented from being erroneously modified. For example, in the case where the inflatable cuff 10 has a defect or a problem, the neural network NN may be erroneously modified. However, the present apparatus 8 can prevent this and can accurately determine EBP values.

The control device 28 controls a display device 32 to concurrently display a trend graph of the thus determined estimated BP values EBP, together with respective trend graphs of the pulse period values RR and the pulse-wave-area-relating values VR, along a common horizontal axis indicative of time, so that those three trend graphs can be compared with one another by a medical person, such as a doctor or a nurse, who attend to the patient.

A BP-measurement starting means or circuit 88 starts a BP-measurement of the BP measuring means 70, when the absolute value of at least one value based on at least one estimated BP value EBP is not smaller than a reference value. A value based on each estimated BP value EBP may be the each value EBP itself, or a change value that is an amount of change of the each value EBP from a "control" value EBP determined at the time of the last BP measuring operation, or the ratio of the amount of change to the "control" value EBP. The BP-measurement starting means 88 includes an EBP-abnormality judging means or circuit for judging that each estimated BP value EBP determined by the EBP determining means 82 is abnormal when at least one value based on at least one value EBP including the each value EBP does not fall within a reference range. When the EBP-abnormality judging means judges that an estimated BP value EBP is abnormal, the BP-measurement starting means 88 starts a BP measurement of the BP measuring means 70.

Next, there will be described the operation of the control device 28 of the BP estimation apparatus 8 by reference to the flow charts of FIGS. 7 and 8. The flow chart of FIG. 7 represents the BP measuring routine; and the flow chart of FIG. 8 represents the EBP determining routine.

Figure 7:
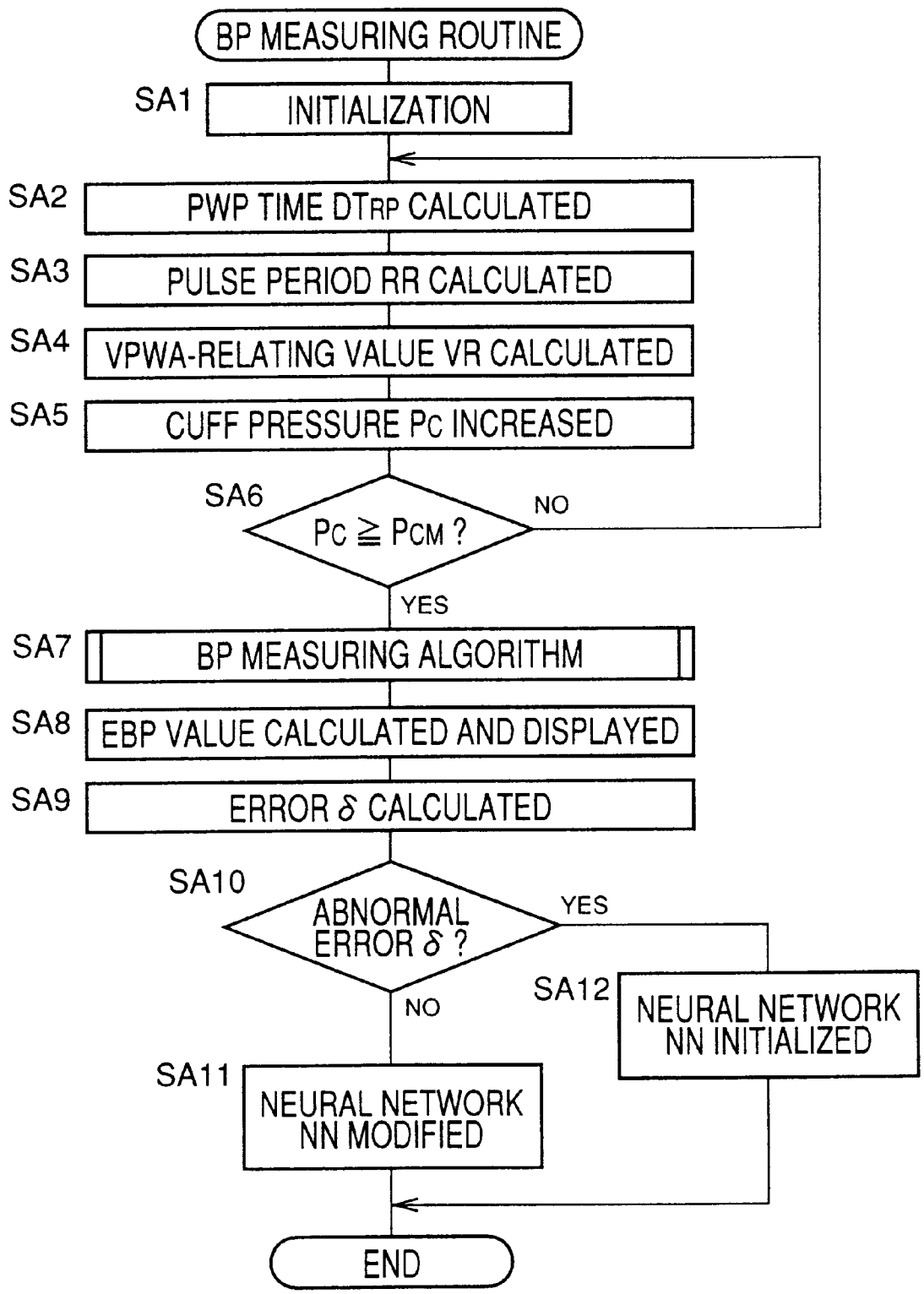
FIG. 7 is a flow chart representing a control program according to which the control device of the apparatus of FIG. 1 is operated for measuring, using an inflatable cuff, a BP value of a living subject.
Figure 8:
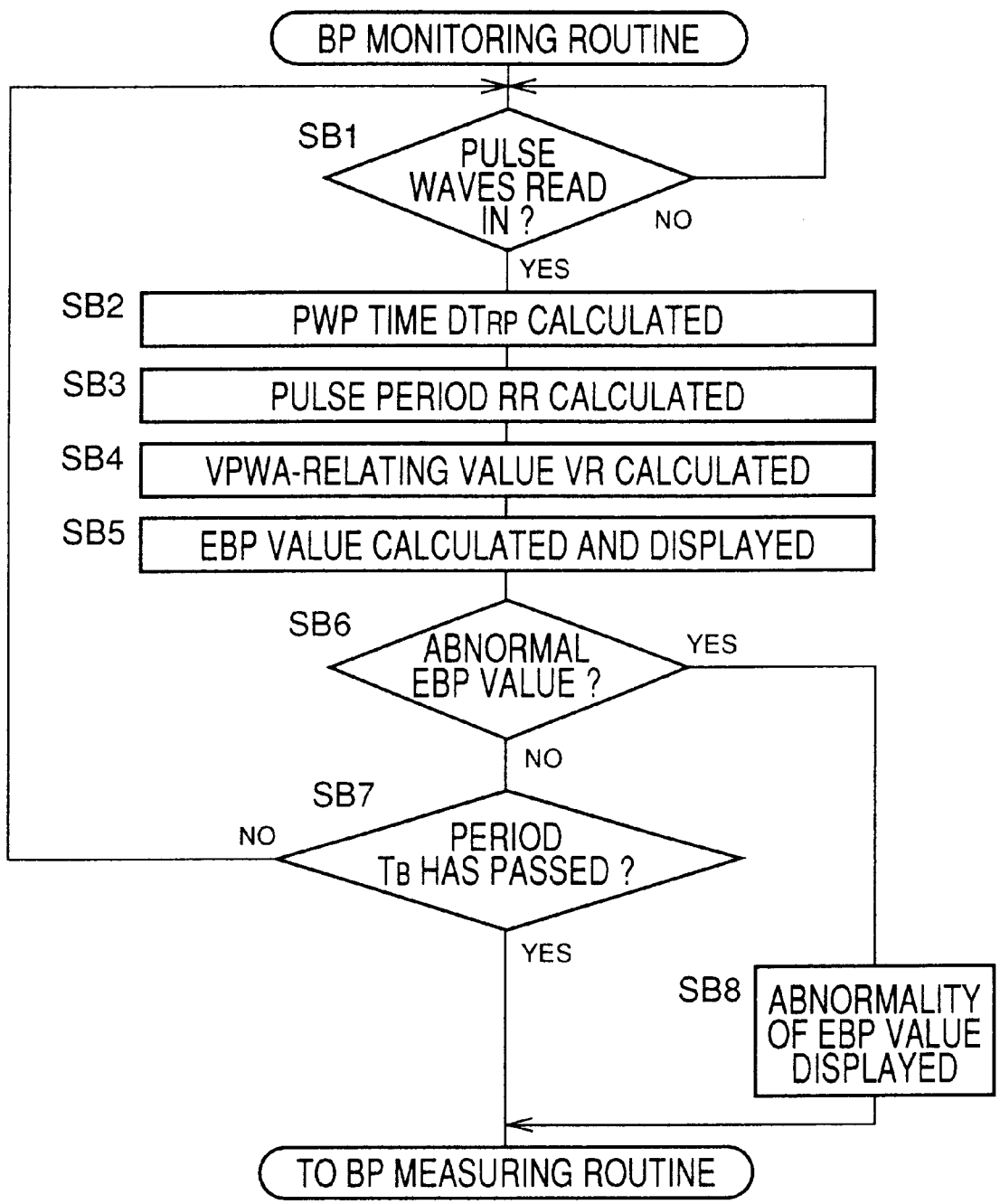
FIG. 8 is a flow chart representing another control program according to which the control device of the apparatus of FIG. 1 is operated for determining an estimated BP value EBP of the living subject.

When a start button (not shown) on the BP estimation apparatus 8 is operated, or when a BP measurement is demanded as a result of execution of the EBP determining routine of FIG. 8, the control of the CPU 29 first carries out Step SA1 of the flow chart of FIG. 7, where timers (or counters) and and registers (not shown) are reset, that is, the initialization of the control device 28 is carried out. Step SA1 is followed by Step SA2 to calculate, as a PWP time value $DT_{RP}$, a time difference between a R-wave of the waveform of a heartbeat-synchronous pulse of the ECG pulse wave and a rising point of the waveform of a corresponding pulse of the PPW which are obtained immediately before the increasing of the cuff pressure. Step SA2 corresponds to the PWP-relating-information obtaining means 74.

Step SA2 is followed by Steps SA3 and SA4 corresponding to the circulation-relating-information obtaining means 76. At Step SA3 corresponding to the heartbeat-relating-information obtaining means 78, the CPU 29 calculates a pulse period value RR (sec) based on the time interval between two successive pulses of the ECG pulse wave, and at Step SA4 corresponding to the VPWA-relating-information obtaining means 80, the CPU 29 calculates a ratio VR (=VP/RR) of an area VP of one pulse of the PPW to the pulse period RR calculated at Step SA3. The ratio VR is indicative of an average amplitude of the one pulse of the PPW.

The control of the CPU 29 goes to Steps SA5 and SA6 corresponding to the cuff-pressure control means 72. At Step SA5, the CPU 29 quickly increases the cuff pressure $P_C$ for a BP measurement of the BP measuring means 70, by switching the selector valve 16 to the inflation position and operating the air pump 18. Step SA5 is followed by Step SA6 to judge whether or not the cuff pressure $P_C$ is equal to or greater than a predetermined target pressure value $P_{CM}$ (e.g., 180 mmHg). If a negative judgement is made at Step SA6, the control of the CPU 29 goes back to Step SA2 so as to continue increasing the cuff pressure $P_C$.

If a positive judgement is made at Step SA6, the control of the CPU 29 goes to Step SA7 to carry out a BP measuring algorithm. More specifically described, the air pump 18 is stopped and the selector value 16 is switched to the slow-deflation position where the valve 16 permits the pressurized air to be slowly discharged from the cuff 10. A systolic BP value $BP_{SYS}$, a mean BP value $BP_{MEAN}$, and a diastolic BP value $BP_{DIA}$ are determined, according to a well known oscillometric BP determining algorithm, based on the variation of respective amplitudes of heartbeat-synchronous pulses of the pulse wave represented by the cuff-pulse-wave signal $SM_1$ obtained while the cuff pressure $P_C$ is slowly decreased at a predetermined rate of about 3 mmHg/sec, and a heart rate HR is determined based on the interval of two successive pulses of the pulse wave. The thus measured BP values and heart rate HR are displayed on the display device 32, and the selector valve 16 is switched to the quick-deflation position where the valve 16 permits the pressurized air to be quickly discharged from the cuff 10. Step SA7 corresponds to the BP measuring means 70.

Step SA7 is followed by Step SA8 corresponding to the EBP determining means 82. At Step SA8, the CPU 29 utilizes a neural network NN which has a three-layer hierarchical structure as shown in FIG. 5 and which has already learned a number of sets of physical information each set of which includes a BP value measured using a data-collect cuff, a PWP time value $DT_{RP}$, a pulse period value RR, and a VPWA-relating value VR all of which are measured when the BP value is measured. The CPU 29 inputs, into the neural network NN, three input signals indicative of the PWP time value $DT_{RP}$, the pulse period value RR, and the VPWA-relating value VR determined at Steps SA2, SA3, SA4, respectively, so that the neural network NN outputs an EBP value. The EBP value output from the neural network NN is displayed on the display device 32.

Step SA8 is followed by Step SA9 where the CPU 29 calculates an error δ as the difference of the BP value (i.e., teacher signal T) measured at Step SA7 and the EBP value determined at Step SA8. Then, at Step SA10, the CPU 29 judges whether the current error δ calculated at Step SA9 in the current control cycle is abnormal. More specifically described, the CPU 29 judges that the current error δ is abnormal, when a state in which the current error δ is greater than the last error δ calculated at Step SA9 in the last control cycle according to the flow chart of FIG. 7 has continued for a predetermined number (e.g., three) of BP measuring operations.

A negative judgment made at Step SA10 means that the modifying of the neural network NN at Step SA11 in the last control cycle is normal or appropriate. In this case, the control of the CPU 29 goes to Step SA12 to modify the connection factors $W_{ij}$, $V_{jk}$ and the offset values $\Theta_j$, $\gamma_k$ so as to reduce the current error δ.

On the other hand, a positive judgment is made at Step SA10 means that the modifying of the neural network NN at Step SA11 in the last control cycle is abnormal or inappropriate. Hence, the control of the CPU 29 goes to Step SA12 corresponding to the network initializing means 86. At Step SA12, the CPU 29 initializes the modified network NN back to the initial neural network NN, i.e., resets the modified connection factors $W_{ij}$, $V_{jk}$ and the modified offset values $\Theta_j$, $\gamma_k$ back to the initial connection factors $W_{ij}$, $V_{jk}$ and the initial offset values $\Theta_j$, $\gamma_k$ before the neural network NN is modified for each individual patient.

After the BP measuring routine of FIG. 7, the control of the CPU 29 goes to the EBP determining routine of FIG. 8. First, at Step SB1, the CPU 29 judges whether an R-wave of the waveform of a heartbeat-synchronous pulse of the ECG pulse wave and a rising point of the waveform of a corresponding pulse of the photoelectric pulse wave ("PPW") have been read in. If a negative judgment is made at Step SB1, the control of the CPU 29 waits until a positive judgment is made at Step SB1.

On the other hand, if a positive judgment is made at Step SB1, the control of the CPU 29 goes to Step SB2, SB3, and SB4 which are similar to Steps SA2, SA3, and SA4 of FIG. 7, respectively, and which correspond to the PWP-relating-information obtaining means 74, the heartbeat-relating-information obtaining means 78, the VPWA-relating-information obtaining means 80, respectively. Thus, the CPU 29 calculates a PWP time value $TD_{RP}$, a pulse period value RR, and a VPWA-relating value VR based on the respective pulses of the ECG pulse wave and the PPW read in at Step SB1.

Step SB4 is followed by Step SB5 corresponding to the EBP determining means 82. At Step SB5, the CPU 29 inputs, into the neural network NN whose connection factors $W_{ij}$, $V_{jk}$ and offset values $\Theta_j$, $\gamma_k$ have been modified at Step SA11 or initialized at Step SA12, three input signals, that is, the PWP time value $TD_{RP}$, the pulse period value RR, and the VPWA-relating value VR calculated at Steps SB2, SB3, SB4, so that the neural network NN outputs an EBP value. The EBP value output from the neural network NN is displayed on the display device 32.

Step SB5 is followed by Step SB6 to judge whether the EBP value determined at Step SB5 is abnormal. If a positive judgment is made at Step SB6, the control of the CPU 29 goes via Step SB8 to the BP measuring routine of FIG. 7. Step SB6 corresponds to the BP-measurement starting means 88. More specifically described, at SB6, the CPU 29 judges that the "current" EBP value determined at Step SB5 in the current control cycle is abnormal, when the absolute value of the ratio of the amount of change of the current EBP value from the "control" EBP value determined at Step SA8 at the time of the last BP measuring operation, to the "control" EBP value, is greater than a predetermined reference value, e.g., 25%, after the absolute value of the ratio determined for each of not less than nineteen prior values EBP has been found as being greater than the reference value. Since the absolute value of the ratio determined for each EBP value is compared with the reference value (e.g., 25%), the reference value defines, in fact, a predetermined reference range (e.g., the range of from −25% to +25%).

If a negative judgment is made at Step SB6, the control of the CPU 29 goes to Step SB7 where the CPU 29 judges whether a predetermined period $T_{BP}$ (e.g., 20 minutes) has passed after the last BP measuring operation was carried out at Step SA7 of FIG. 7. If a negative judgment is made at Step SB7, the control of the CPU 29 goes back to Step SB1 and the following steps so as to carry out the EBP determining routine, that is, determine an EBP value for each of successive heartbeat-synchronous pulses, and display, on the display device 32, the trend graph of the determined EBP values. On the other hand, if a positive judgment is made at Step SB7, the control of the CPU 29 goes back to the BP measuring routine of FIG. 7 so as to measure a BP value of the patient using the cuff 10 and modify the neural network NN.

If a positive judgment is made at Step SB6, the control of the CPU 29 goes to Step SB8. At Step SB8, the CPU 29 displays the abnormality of the EBP value calculated at Step SB5, on the display device 32. Then, the control of the CPU 29 goes back to the BP measuring routine of FIG. 7 so as to measure an accurate BP value of the patient using the cuff 10.

In the present embodiment, the EBP determining means 82 employs the neural network NN which has learned a number of sets of physical information each set of which includes a BP value measured from a living subject using a cuff which may, or may not, be identical with the cuff 10, and a PWP time value $DT_{RP}$, a pulse period value RR, and a VPWA-relating value VR which are measured from that subject when the BP value is measured. The EBP determining means 82 inputs, into the neural network NN, three input signals, i.e., each PWP time value $DT_{RP}$, each pulse period value RR, and each VPWA-relating value VR which are iteratively measured from the patient, so that the neural network NN iteratively outputs an EBP value. The thus obtained EBP value enjoys a higher estimation accuracy, because the EBP value is determined based on not only each PWP time value $DT_{RP}$ but also each pulse period value RR as a BP-dependent variable parameter relating to the central part of the circulatory system of the patient and each VPWA-relating value VR as another BP-dependent variable parameter relating to a peripheral part of the circulatory system of the patient.

In addition, in the present embodiment, when the BP measuring means 70 measures a BP value of the patient, the network modifying means 84 modifies the neural network NN of the EBP determining means 82, based on the comparison (i.e., difference or error δ) between the BP value measured by the BP measuring means 70 and the EBP value determined by the EBP determining means 82 or the neural network NN when the BP value is measured by the BP measuring means 70. Thus, the neural network NN which has already learned further learns for adaptation thereof to each individual patient. Accordingly, the present BP estimation apparatus 8 enjoys a higher accuracy of estimation of BP values.

While the present invention has been described in its preferred embodiment, the invention may otherwise be embodied.

For example, although in the illustrated embodiment the EBP determining means 82 determines the EBP value of the patient based on not only the PWP time value $DT_{RP}$ calculated by the PWP-relating-information obtaining means 74 but also the pulse period value RR calculated by the heartbeat-relating-information obtaining means 78 and the VPWA-relating value VR calculated by the VPWA-relating-information obtaining means 80, the EBP determining means 82 may be modified to determine an EBP value of the patient based on not only the PWP time value $DT_{RP}$ but also either one of the pulse period value RR and the VPWA-relating value VR. In the latter case, either one of the pulse period value RR as the heart-relating parameter which changes in relation to the BP of the patient and the VPWA-relating value VR as the peripheral-body-portion-relating parameter which changes in relation to the BP of the patient is used in addition to the PWP time value $DT_{RP}$. Accordingly, the accuracy of estimation of EBP values is improved as compared with the conventional manner in which a BP value of a patient is estimated based on a PWP time value $DT_{RP}$ only.

While in the illustrated embodiment the neural network NN is constituted or provided by software, i.e., a computer program, it is possible that the neural network NN be provided by hardware, i.e., combination of electronic elements.

While in the illustrated embodiment the neural network NN includes the three intermediate-layer units $Y_1, Y_2, Y_3$, it is possible to employ two, four, or more intermediate-layer units. In addition, it is possible to employ two or more intermediate layers.

Although in the illustrated embodiment the network modifying means 84 modifies the connection factors $W_{ij}$, the connection factors $V_{jk}$, the offset values $\Theta_j$, and the offset value $\gamma_k$ each time the BP measuring means 70 measures a BP value of the patient, it is possible to employ a different known neural-network modifying method, such as the collective-modification method or the moment method.

While in the illustrated embodiment the BP measuring means 70 periodically measures a BP value of the patient at the predetermined period $T_B$ and the network modifying means 84 modifies, based on each BP value measured by the BP measuring means 70, the neural network NN, that is, adapts the network NN to an individual patient, it is possible that when the present apparatus 8 is started, the BP measuring means 70 successively measures BP values of an individual patient plural (e.g., five) times. In the latter case, the neural network NN can be more quickly adapted to the patient.

While in the illustrated embodiment the reflection-type PWP detecting probe 38 is used as the volumetric-pulse-wave ("VPW") detecting device, it is possible to employ, as the VPW detecting device, a transmission-type PWP detecting device.

It is to be understood that the present invention may be embodied with other changes, improvements, and modifications that may occur to a person having ordinary skill in the art without departing from the scope and spirit of the invention defined in the appended claims.

What is claimed is:

1. An apparatus for iteratively estimating an intra-arterial blood-pressure value of a living subject, based on information non-invasively obtained from a circulatory system of the subject, the apparatus comprising:

a pulse-wave-propagation-relating-information obtaining device which non-invasively and iteratively obtains a piece of pulse-wave-propagation-relating information relating to propagation of a pulse wave through an arterial vessel of the living subject;

a circulation-relating-information obtaining device which non-invasively and iteratively obtains a piece of circulation-relating information comprising at least one of a piece of heartbeat-relating information relating to heartbeat of the living subject and a piece of pulse-wave-area-relating information relating to area of a heartbeat-synchronous pulse of a volumetric pulse wave obtained from a peripheral body portion of the living subject; and blood-pressure estimating means comprising a neural network which learns a plurality of sets of information each set of which comprises a blood-pressure value measured using an inflatable cuff, a piece of pulse-wave-propagation-relating information obtained when the blood-pressure value is measured using the cuff, and at least one of a piece of heartbeat-relating information obtained when the blood-pressure value is measured using the cuff and a piece of pulse-wave-area-relating information obtained when the blood-pressure value is measured using the cuff, the neural network iteratively estimating an intra-arterial blood-pressure value of the living subject, based on each piece of pulse-wave-propagation-relating information iteratively obtained by the pulse-wave-propagation-relating-information obtaining device and at least one of each piece of heartbeat-relating information and each piece of pulse-wave-area-relating information which is iteratively obtained by the circulation-relating-information obtaining device.

2. An apparatus according to claim 1, further comprising a blood-pressure measuring device which includes an inflatable cuff adapted to apply a pressing pressure to a body portion of the living subject and which measures a blood-pressure value of the living subject by changing the pressing pressure of the inflatable cuff, wherein the blood-pressure estimating means further comprises modifying means for modifying the neural network based on comparison of the blood-pressure value of the living subject measured by the measuring device, and the blood-pressure value of the subject estimated by the blood-pressure estimating means when the blood-pressure value is measured by the blood-pressure measuring device.

3. An apparatus according to claim 1, wherein the neural network learns said plurality of sets of information each set of which comprises the blood-pressure value measured using t he inflatable cuff, the piece of pulse-wave-propagation-relating information obtained when the blood-pressure value is measured using the cuff, the piece of heartbeat-relating information obtained when the blood-pressure value is measured using the cuff, and the piece of pulse-wave-area-relating information obtained when the blood-pressure value is measured using the cuff, and wherein the blood-pressure estimating means iteratively estimates an intra-arterial blood-pressure value of the living subject, based on each piece of pulse-wave-propagation-relating information iteratively obtained by the pulse-wave-propagation-relating-information obtaining device, and each piece of heartbeat-relating information and each piece of pulse-wave-area-relating information which are iteratively obtained by the circulation-relating-information obtaining device.

4. An apparatus according to claim 1, wherein the neural network comprises an input layer including at least two input-layer elements, at least one intermediate layer including at least two intermediate-layer elements, and an output layer including an output-layer element, each of the input-layer elements being connected to each of the intermediate-layer elements, with a corresponding one of a plurality of first connection factors, each of the intermediate-layer elements being connected to the output-layer element, with a corresponding one of a plurality of second connection factors, and wherein when a value is transferred from said each input-layer element to said each intermediate-layer element, the value is multiplied with said one first connection factor and then is plus a corresponding one of first offset values, and when a value is transferred from said each intermediate-layer element to the output-layer element, the value is multiplied with said one second connection factor and then is plus a corresponding one of second offset values.

5. An apparatus according to claim 4, wherein each of the intermediate-layer elements outputs an output value based on a sum of respective input values received from the input-layer elements and a first transfer function, and the output-layer element outputs an output value based on a sum of respective input values received from the intermediate-layer elements and a second transfer function.

6. An apparatus according to claim 4, further comprising a blood-pressure measuring device which includes an inflatable cuff adapted to apply a pressing pressure to a body portion of the living subject and which measures a blood-pressure value of the living subject by changing the pressing pressure of the inflatable cuff, wherein the blood-pressure estimating means further comprises modifying means for modifying the first and second connection factors and the first and second offset values of the neural network based on a difference of the blood-pressure value of the living subject measured by the blood-pressure measuring device, and the blood-pressure value of the subject estimated by the blood-pressure estimating means when the blood-pressure value is measured by the blood-pressure measuring device.

7. An apparatus according to claim 6, wherein the blood-pressure estimating means further comprises initializing means for initializing the modified first and second connection factors and the modified first and second offset values of the neural network, to the first and second connection factors and the first and second offset values before being modified by the modifying means, when a state in which a difference of a current blood-pressure value measured by the measuring device and a blood-pressure value estimated by the blood-pressure estimating means when the current blood-pressure value measured by the measuring device is greater than a difference of a preceding blood-pressure value measured by the measuring device and a blood-pressure value estimated by the blood-pressure estimating means when the preceding blood-pressure value is measured by the measuring device, continues for a predetermined number of blood-pressure measurements of the blood-pressure measuring device.

8. An apparatus according to claim 1, further comprising:

a blood-pressure measuring device which includes an inflatable cuff adapted to apply a pressing pressure to a body portion of the living subject and which measures a blood-pressure value of the living subject by changing the pressing pressure of the inflatable cuff; and starting means for starting a blood-pressure measurement of the blood-pressure measuring device when the blood-pressure value of the living subject estimated by the blood-pressure estimating means is abnormal.

9. An apparatus according to claim 1, further comprising an informing device which informs a user of an occurrence of an abnormality to the blood pressure of the living subject, when the blood-pressure value of the living subject estimated by the blood-pressure estimating means is abnormal.

10. An apparatus according to claim 1, wherein the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

11. An apparatus according to claim 1, wherein the pulse-wave-propagation-relating-information obtaining device comprises an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a body portion of the living subject, and which emits a light toward the body portion and obtains a photoelectric pulse wave including a plurality of heartbeat-synchronous pulses, from the light received from the body portion.

12. An apparatus according to claim 11, wherein the circulation-relating-information obtaining device comprises a heartbeat-relating-information obtaining device which non-invasively and iteratively obtains a piece of heartbeat-relating information, and wherein the heartbeat-relating-information obtaining device comprises pulse-period calculating means for iteratively calculating, as the piece of heartbeat-relating information, a pulse period equal to an interval between each pair of successive heartbeat-synchronous pulses of the electrocardiographic pulse wave detected by the electrocardiographic-pulse-wave detecting device.

13. An apparatus according to claim 11, wherein the circulation-relating-information obtaining device comprises a pulse-wave-area-relating-information obtaining device which non-invasively and iteratively obtains a piece of pulse-wave-area-relating information, and wherein the pulse-wave-area-relating-information obtaining device comprises ratio calculating means for iteratively calculating, as the piece of pulse-wave-area-relating information, a ratio of an area defined by a waveform of each heartbeat-synchronous pulse of the photoelectric pulse wave as the volumetric pulse wave to a pulse period equal to an interval between each pair of successive heartbeat-synchronous pulses of the electrocardiographic pulse wave detected by the electrocardiographic-pulse-wave detecting device.

* * * * *